US011959102B2

(12) United States Patent
O'Heeron et al.

(10) Patent No.: US 11,959,102 B2
(45) Date of Patent: Apr. 16, 2024

(54) AUGMENTATION OF FIBROBLAST REGENERATIVE ACTIVITY

(71) Applicant: Figene, LLC, Houston, TX (US)

(72) Inventors: Pete O'Heeron, Houston, TX (US); Thomas Ichim, San Diego, CA (US)

(73) Assignee: Figene, LLC, Houston, TX (US)

( * ) Notice: Subject to any disclaimer, the term of this patent is extended or adjusted under 35 U.S.C. 154(b) by 327 days.

(21) Appl. No.: 16/770,495

(22) PCT Filed: Dec. 17, 2018

(86) PCT No.: PCT/US2018/065931
§ 371 (c)(1),
(2) Date: Jun. 5, 2020

(87) PCT Pub. No.: WO2019/125996
PCT Pub. Date: Jun. 27, 2019

(65) Prior Publication Data
US 2021/0180020 A1 Jun. 17, 2021

Related U.S. Application Data

(60) Provisional application No. 62/608,031, filed on Dec. 20, 2017.

(51) Int. Cl.
*C12N 5/077* (2010.01)
*A61K 33/00* (2006.01)

(52) U.S. Cl.
CPC ............ *C12N 5/0656* (2013.01); *A61K 33/00* (2013.01); *C12N 2500/02* (2013.01); *C12N 2500/05* (2013.01)

(58) Field of Classification Search
None
See application file for complete search history.

(56) References Cited

U.S. PATENT DOCUMENTS

| 11,034,934 | B2* | 6/2021 | O'Heeron | C12N 5/0656 |
| 2009/0011051 | A1 | 1/2009 | Roth et al. | |
| 2009/0169623 | A1 | 7/2009 | Sene et al. | |
| 2012/0282353 | A1 | 11/2012 | Roth et al. | |
| 2017/0354830 | A1 | 12/2017 | Moffett | |
| 2021/0309971 | A1* | 10/2021 | O'Heeron | A61P 19/08 |
| 2021/0393700 | A1* | 12/2021 | O'Heeron | A61K 35/16 |

FOREIGN PATENT DOCUMENTS

| CN | 105624117 | 6/2016 |
| JP | 2009-537466 | 10/2009 |
| WO | WO 2007/131677 | 11/2007 |
| WO | 2010/007247 A2 | 1/2010 |
| WO | 2018/132594 A1 | 7/2018 |
| WO | 2018/195308 A1 | 10/2018 |

OTHER PUBLICATIONS

Spitz et al., Methods in Molecular Biology, 2010, v.610, pp. 183-199.*
Bohrn et al., Procedia Engineering, 2010, v.5 pp. 17-20.*
Pufe et at., J of Pathology, 2003, v.200, pp. 130-136.*
Saed et al., Fertility and Sterility, 2002, v.78 pp. 137-143.*
Kang et al. "Effect of Hyperbaric Oxygen on the Growth Factor Profile of Fibroblasts," Archives of Facial Plastic Surgery, Jan. 1, 2004 (Jan. 1, 2004), vol. 6, Iss. 1, pp. 31-35.
Kuwano et al. "Analysis of Nitric Oxide-Stabilized mRNAs in Human Fibroblasts Reveals HuR-Dependent Heme Oxygenase 1 Upregulation," Molecular and Cellular Biology, May 1, 2009 (May 1, 2009), vol. 29, No. 10, pp. 2622-2635.
Ichim et al. "Fibroblasts as a Practical Alternative to Mesenchymal Stem Cells," Journal of Translational Medicine, Jul. 27, 2018 (Jul. 27, 2018), vol. 16, Issue 1, pp. 1-9.
English translation of Office Communication issued in Japanese Patent Application No. 2020-534217, dated Oct. 28, 2022.
Abraham, N. G. et al., "Pharmacological and Clinical Aspects of Heme Oxygenase", Pharmacological Reviews, vol. 60, No. 1, Mar. 6, 2008 (Mar. 6, 2008), pp. 79-127.
Allanson, Munif et al: "Immunoprotective UVA (320-400 nm) Irradiation Upregulates Heme Oxygenase-1 in the Dermis and Epidermis of Hairless Mouse Skin", Journal of Investigative Dermatology, vol. 122, No. 4, Apr. 1, 2004 (Apr. 1, 2004), pp. 1030-1036.
Choi, Yoon Kyung et al: "Carbon Monoxide Promotes VEGF Expression by Increasing HIF-I[alpha] Protein Level via Two Distinct Mechanisms, Translational Activation and Stabilization of HIF-I[alpha] Protein", Journal of Biological Chemistry, vol. 285, No. 42, Oct. 1, 2010 (Oct. 1, 2010), pp. 32116-32125.
Li, Bao-Zhu et al: "Therapeutic Potential of H0-1 in Autoimmune Diseases", Inflammation, vol. 37, No. 5, May 13, 2014 (May 13, 2014), pp. 1779-1788, Plenum Press, New York, NY, US.
Lin, Heng-Huei et al: "Heme Oxygenase-1/Carbon Monoxide Induces Vascular Endothelial Growth Factor Expression via p38 Kinase-dependent Activation of Spl", Journal of Biological Chemistry, vol. 286, No. 5, Feb. 1, 2011 (Feb. 1, 2011), pp. 3829-3838.
Nakamura et al., "Attenuation of Transforming Growth Factor-[beta]-Stimulated Collagen Production in Fibroblasts by Quercetin-Induced Heme Oxygenase-1", American Journal of Respiratory Cell and Molecular Biology., vol. 44, No. 5, May 1, 2011 (May 1, 2011), pp. 614-620.
Panchenko et al: "Induction of heme oxygenase-1 by hypoxia and free radicals in human dermal fibroblasts", American Journal of Physiology Cell Physiology, vol. 278, No. I, Jan. 1, 2000 (Jan. 1, 2000), pp. C92-C101.
Steinbrech et al: "Fibroblast Response to Hypoxia: The Relationship between Angiogenesis and Matrix Regulation", Journal of Surgical Research, vol. 84, No. 2, Jun. 1, 1999 (Jun. 1, 1999), pp. 127-133.

(Continued)

*Primary Examiner* — Michail A Belyavskyi
(74) *Attorney, Agent, or Firm* — Norton Rose Fulbright US LLP

(57) ABSTRACT

Embodiments of the disclosure include methods and compositions for use of prepared fibroblasts and/or conditioned media therefrom. In particular embodiments, the prepared fibroblasts have enhanced regenerative and may have an increase in secretion of one or more cytokines and/or growth factors; may have an increase in anti-apoptotic activity; and/or may have a modulated immunogenicity. In specific embodiments, the fibroblasts are prepared by exposure to hypoxia and/or carbon monoxide.

17 Claims, 2 Drawing Sheets

(56) References Cited

OTHER PUBLICATIONS

Steinbrech et al: "Hypoxia Upregulates VEGF Production in Keloid Fibroblasts", Annals of Plastic Surgery., vol. 42, No. 5, May 1, 1999 (May 1, 1999), pp. 514-520.
English translation of Office Communication issued in Chinese Patent Application No. 2018800865008, dated Apr. 10, 2023.
Kim et al., "Heat shock protein-70 mediates the cytoprotective effect of carbon monoxide: involvement of p38 beta MAPK and heat shock factor-1," Journal of Immunology, 175(4):2622-2629, 2005.
Zhao et al., "Mechanism of carbon monoxide affecting the expression of cellular adhesion molecule under stimulation of inflammatory cytokines to human gingival fibroblasts," West China Journal o Stomatology, 31(4):420-424, 2013. (English abstract).

* cited by examiner

AUGMENTATION OF FIBROBLAST REGENERATIVE ACTIVITY

CROSS-REFERENCE TO RELATED APPLICATIONS

This application is a national phase application under 35 U.S.C. § 371 that claims priority to International Application No. PCT/US2018/065931 filed Dec. 17, 2018, which claims priority to U.S. Provisional Application No. 62/608,031 filed Dec. 20, 2017, all of which are incorporated herein by reference in their entirety.

TECHNICAL FIELD

Embodiments of the disclosure concern at least the fields of cell biology, molecular biology, biochemistry, cell therapy, and medicine.

BACKGROUND

One of the primary functions of a fibroblast is to maintain the structural integrity of connective tissues by continuously secreting precursors of the extracellular matrix. A fibroblast secretes precursors of all components of the extracellular matrix, primarily the ground substance and a variety of fibers or structural proteins. They also secrete small molecular weight diffusible factors that influence and coordinate the function and product of neighboring cells to enhance tissue response. The composition of the extracellular matrix significantly determines the physical properties of connective tissues. Fibroblasts are involved in many processes within the body. Wound healing is a complex process requiring the combined activation of numerous processes including the modulation of fibroblast activity. During the wound healing process, dermal fibroblasts migrate to the wound bed where wound cell-secreted Transforming Growth Factor-1 matrix molecules (e.g., a fibronectin splice variant) and mechanical cues (i.e., matrix tension) initiate their differentiation into myofibroblasts. Myofibroblasts can be distinguished from dermal fibroblasts as they express smooth muscle alpha-actin, contain bundles of contractile microfilaments, and have extensive cell-to-matrix attachment sites. The myofibroblasts synthesize, deposit and remodel the extracellular matrix to form granulation tissue, and thereby contract the wound. The connective tissue that forms during the healing process is often fibrous in nature, and commonly forms into a connective tissue scar by a process known as fibrosis. Known in the art are methods of treatment using autologous fibroblasts (i.e. fibroblast obtained from a donor who will also be the recipient of cultured fibroblasts). Among the known uses of such fibroblasts are a method of promoting healing of wounds, such as an epithelial wound or fistula, by administering cultured fibroblasts; a method of corrective surgery by the augmentation of tissue sub-adjacent to a vocal cord defect; and a method of treatment of vocal fold scarring and repair of skin and soft tissue defects. Despite numerous possibilities for utilization of fibroblasts in regenerative medicine, currently factors limiting fibroblast therapeutic utilization is lack of means of optimizing regenerative activity of fibroblasts. The present disclosure provides a solution for this need.

BRIEF SUMMARY

Embodiments of the disclosure include methods and compositions directed to preparation of fibroblasts such that they have one or more attributes that are lacking in fibroblasts not so prepared. In particular embodiments, the fibroblasts are prepared to have enhanced regenerative properties. In specific embodiments, the fibroblasts have an increase in secretion of one or more cytokines and/or one or more growth factors, they have an increase in anti-apoptotic activity, and/or the immunogenicity of the fibroblasts is modulated. In specific embodiments fibroblasts are exposed by hypoxia and/or carbon monoxide in sufficient levels such that the regenerative capacity of the fibroblasts becomes enhanced compared to fibroblasts that have not been similarly exposed to hypoxia and/or carbon monoxide in sufficient levels.

In some embodiments, fibroblasts and/or media conditioned therefrom are provided to an individual in need thereof. In specific embodiments, the individual has a medical condition requiring replenishing of cells or tissues following the medical condition, including at a localized site in some cases. The conditioned media may comprise one or more growth factors, one or more cytokines, one or more peptides, one or more proteins and/or combinations thereof.

Embodiments of the disclosure include a method of enhancing a therapeutic activity of a plurality of fibroblasts, comprising the step of providing to the fibroblasts an effective amount of one or more agents and/or one or more conditions that comprise stimulation of native heme oxygenase (HO)-1 expression in the fibroblasts, exposure of the fibroblasts to exogenously provided HO-1, and/or expression of HO-1 from an exogenously provided vector in the fibroblasts. In specific embodiments, the therapeutic activity comprises regenerative activity of the fibroblasts. The fibroblasts may have an increase in secretion of one or more cytokines and/or one or more growth factors; the fibroblasts may have an increase in anti-apoptotic activity; and/or the immunogenicity of the fibroblasts is modulated, such as reduced or increased. In particular embodiments, the one or more agents and/or conditions comprises hypoxia, carbon monoxide, or a combination thereof. The carbon monoxide may be provided to the fibroblasts subsequent to the hypoxia. The carbon monoxide may be provided to the fibroblasts at the same time as the hypoxia.

In particular embodiments, an effective amount of the fibroblasts and/or conditioned medium therefrom is provided to an individual. The individual may have a medical condition for which fibroblasts and/or conditioned medium therefrom is therapeutic, allowing improvement of at least one symptom, for example. In specific embodiments, the medical condition is an autoimmune disease, degenerative disease, inflammatory disease, and/or a fibrotic disease. The conditioned medium may comprise one or more growth factors and/or one or more cytokines. The hypoxia may be 0.1%-10%, 0.1%-5%, 0.1%-2.5%, or 0.1%-1% oxygen, for example. In specific embodiments, the hypoxia occurs for a period of time that is at least or no more than between 30 minutes-3 days, although in some cases it may be less than 30 minutes or greater than 3 days. The fibroblasts may be exposed to one or more growth factors prior to and/or during exposure to hypoxia, carbon monoxide, or a combination thereof.

In one embodiment there is a method of preparing fibroblasts, comprising the step of exposing fibroblasts to an effective amount of hypoxia, carbon monoxide, or both. In a specific embodiment, the fibroblasts are exposed to hypoxia and carbon monoxide at the same time. In specific embodiments, the fibroblasts are exposed to hypoxia and carbon monoxide at a different time. In some cases, the fibroblasts are exposed to hypoxia before the exposure to carbon monoxide. In particular cases, the fibroblasts and/or conditioned media therefrom are provided in an effective amount to an individual in need thereof. The individual may have an autoimmune disease, degenerative disease, inflammatory disease, and/or a fibrotic disease.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawing, in which.

DETAILED DESCRIPTION

Figure 1:
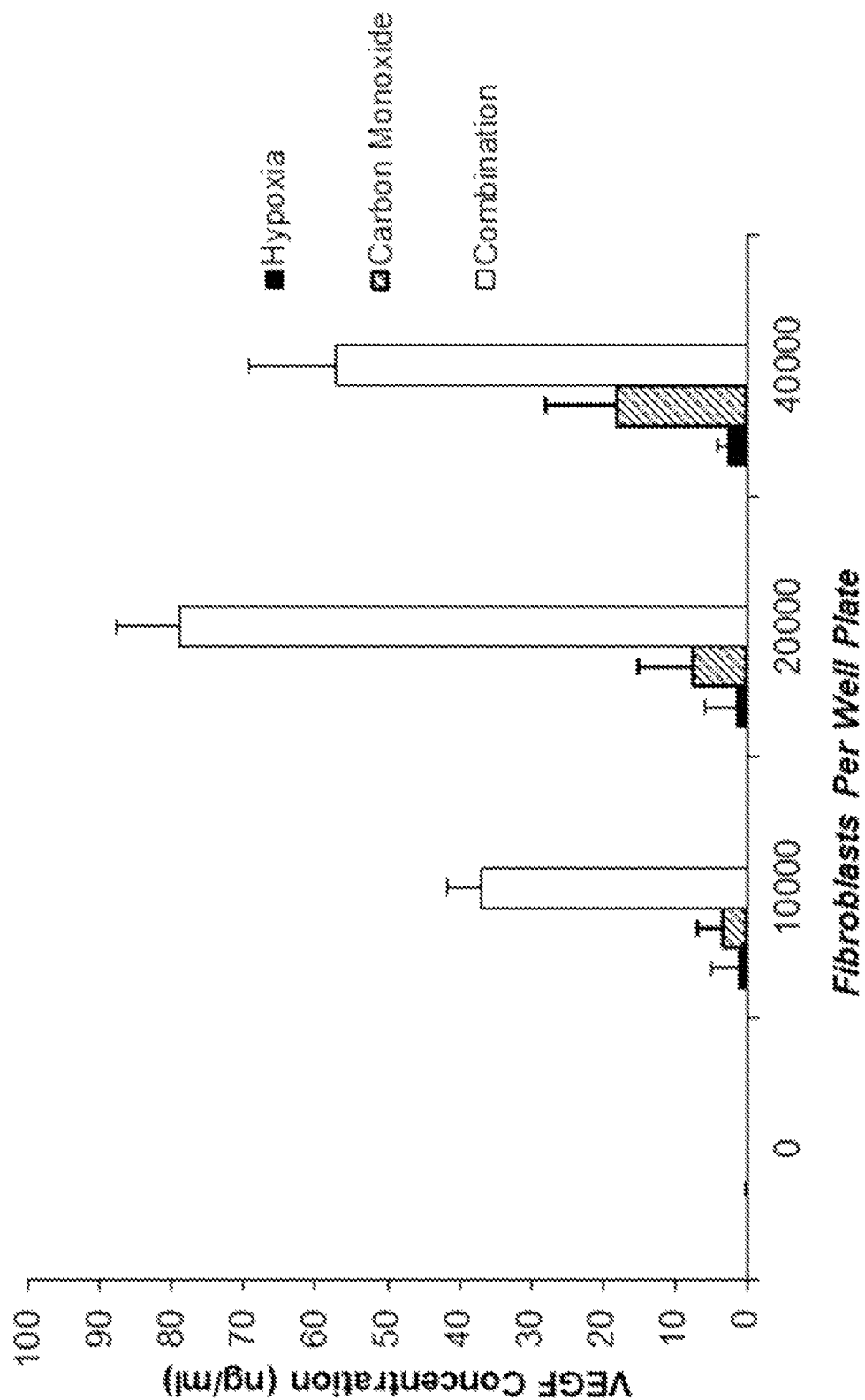
FIG. 1 shows stimulation of VEGF production by culture of fibroblasts with hypoxia, carbon monoxide, or hypoxia followed by carbon monoxide.

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the disclosure may "consist essentially of" or "consist of" one or more sequences of the disclosure, for example. Some embodiments of the disclosure may consist of or consist essentially of one or more elements, method steps, and/or methods of the disclosure. It is contemplated that any method or composition described herein can be implemented with respect to any other method or composition described herein. Embodiments discussed in the context of methods and/or compositions of the disclosure may be employed with respect to any other method or composition described herein. Thus, an embodiment pertaining to one method or composition may be applied to other methods and compositions of the disclosure as well.

The present disclosure pertains at least to the field of cellular therapy, more specifically, the disclosure pertains to augmentation of fibroblast regenerative activity through culture under specific culture conditions to enhance the regenerative activity of the fibroblasts themselves. The disclosure further pertains to modification of one or more cellular culture conditions to induce cellular programs capable of increasing therapeutic activity of fibroblasts. As used herein, the term "regenerative activity" is defined as the ability to generate cells and tissues de novo, in some embodiments.

In certain embodiments, there are methods of enhancing one or more therapeutic activities of a plurality of fibroblasts by providing to the fibroblasts an effective amount of one or more agents or conditions that enhances the activity or activities, such as regenerative activity for the fibroblasts. The modified fibroblasts having greater regenerative activity compared to the activity in the absence of being modified may then be utilized for a variety of purposes, such as therapeutic uses of the cells, including in a mammal, such as a human, dog, cat, horse, cow, and so forth.

I. Fibroblasts, Modifications Thereto, and Methods of Producing

Disclosed are methods and compositions related to enhancement of therapeutic activity of fibroblasts in a regenerative capacity. In specific embodiments, fibroblasts are enhanced through stimulation of heme oxygenase (HO)-1 expression by one or more agents and/or conditions, and the stimulation may or may not be direct. Such enhancement may occur through (1) exposure of the fibroblasts to one or more agents and/or conditions that increase endogenous expression of HO-1; (2) exposure of the fibroblasts to exogenously provided HO-1; and/or (3) exposure of the fibroblasts to exogenously provided HO-1 upon expression of HO-1 from an exogenously provided vector in the fibroblasts that express HO-1, for example. In specific embodiments, the one or more agents includes carbon monoxide (CO), hypoxia, or a combination thereof. In certain embodiments when both CO and hypoxia are provided to the fibroblasts, the order of their exposure is particular. In some cases, they are provided to the fibroblasts at the same time, whereas in other cases they are provided to the fibroblasts at different times, and in some cases they are both provided to the cells at separate times and at the same time. In some cases, the CO is provided to the fibroblasts before the hypoxia, whereas in other cases the CO is provided to the fibroblasts after the hypoxia.

In some embodiments, there are methods of treating fibroblast cells to enhance their regenerative activity, comprising the steps of: a) optionally obtaining a fibroblast population (the fibroblasts may be obtained by another party or obtained from storage or commercially obtained, for example); b) priming the fibroblast population by exposure to hypoxia for a sufficient time period, for example to induce upregulation of hypoxia inducible factor (HIF)-1 alpha; and c) optionally subsequent to exposure to hypoxia, treating the fibroblasts with CO at a sufficient concentration and time period to induce upregulation of HO-1.

In particular embodiments, fibroblasts are enhanced by methods encompassed herein in their activity for cytokine secretion, upregulation of anti-apoptotic properties, and/or modulation of immunogenicity. In specific embodiments, the regenerative activity comprises enhanced production of one or more cytokines, such as cytokines selected from the group consisting of a) fibroblast growth factor (FGF)-1; b) FGF-2; c) FGF-5; d) FGF-12; e) IL-10; f) leukemia inhibitor factor; f) insulin growth factor; g) epidermal growth factor; h) vascular endothelial growth factor (VEGF); and i) a combination thereof.

Although the regenerative activity may be of any kind, in specific embodiments the regenerative activity comprises the ability for the fibroblasts to differentiate into any other type of cell including at least into chondrocytes; adipocytes; and/or osteocytes.

In some embodiments, a regenerative activity comprises an ability of the fibroblasts to produce a conditioned media that is mitogenic for any type of cell, including at least fibroblasts; mesenchymal stem cells; notochord cells; and/or chondrocytic progenitors cells, for example.

In particular embodiments, fibroblasts have an enhanced regenerative activity following exposure to one or more certain conditions, including exposure of a condition for a certain period of time or other form of parameter for the condition. In specific embodiments, fibroblasts are exposed to a hypoxic environment. As an example, incubation of fibroblasts in a hypoxic environment may be performed under conditions of at least or no more than 0.1%-10% oxygen; 0.1%-9%; 0.1%-8%; 0.1%-7%; 0.1%-6%; 0.1%-5%; 0.1%-4%; 0.1%-3%; 0.1%-2%; 0.1%-1%; 0.1%-0.75%; 0.1%-0.5%; 0.25%-10%; 0.25%-9%; 0.25%-8%; 0.25%-7%; 0.25%-6%; 0.25%-5%; 0.25%-4%; 0.25%-3%; 0.25%-2%; 0.25%-1%; 0.25%-0.75%; 0.25%-0.5%; 0.5%-10%; 0.5%-9%; 0.5%-8%; 0.5%-7%; 0.5%-6%; 0.5%-5%; 0.5%-4%; 0.5%-3%; 0.5%-2%; 0.5%-1%; 0.5%-0.75%; 0.75%-10%; 0.75%-9%; 0.75%-8%; 0.75%-7%; 0.75%-6%; 0.75%-5%; 0.75%-4%; 0.75%-3%; 0.75%-2%; 0.75%-1%; 1%-9%; 1%-8%; 1%-7%; 1%-6%; 1%-5%; 1%-4%; 1%-3%; 1%-2%; 2%-9%; 2%-8%; 2%-7%; 2%-6%; 2%-5%; 2%-4%; 2%-3%; 3%-9%; 3%-8%; 3%-7%; 3%-6%; 3%-5%; 3%-4%; 4%-9%; 4%-8%; 4%-7%; 4%-6%; 4%-5%; 5%-9%; 5%-8%; 5%-7%; 5%-6%; 6%-9%; 6%-8%; 6%-7%; 7%-9%; 7%-8%; or 8%-9%, 0.1%, 0.2%, 0.3%, 0.4%, 0.5%, 0.6%, 0.7%, 0.8%, 0.9%, 1.0%, 1.25%, 1.5%, 1.75%, 2.0%, 2.25%, 2.5%, 2.75%, 3%, 3.25%, 3.5%, 3.75%, 4.0%, 4.25%, 4.5%, 4.75%, 5%, 5.25%, 5.5%, 5.75%, 6%, 6.25%, 6.5%, 6.75%, 7.25%, 7.5%, 7.75%, 8%, 8.25%, 8.5%, 8.75%, 9%, or 10%, for example.

In some cases exposure of the fibroblasts to the hypoxic environment occurs for a certain period of time, and this time may or may not be continual. In specific embodiments, incubation of fibroblasts in a hypoxic environment occurs for a period of time, such as at least or no more than between 30 minutes (min)-3 days; 30 min-2 days; 30 min-1 days; 30 min-18 hours (hrs); 30 min-12 hrs; 30 min-8 hrs; 30 min-6 hrs; 30 min-4 hrs; 30 min-2 hrs; 30 min-1 hr; 45 min-3 days; 45 min-2 days; 45 min-1 days; 45 min-18 hrs; 45 min-12 hrs; 45 min-8 hrs; 45 min-6 hrs; 45 min-4 hrs; 45 min-2 hrs; 45 min-1 hr; 60 min-3 days; 60 min-2 days; 60 min-1 days; 60 min-18 hrs; 60 min-12 hrs; 60 min-8 hrs; 60 min-6 hrs; 60 min-4 hrs; 60 min-2 hrs; 60 min-1 hr; 2 hrs-3 days; 2 hrs-2 days; 2 hrs-1 days; 2 hrs-18 hrs; 2 hrs-12 hrs; 2 hrs-8 hrs; 2 hrs-6 hrs; 2 hrs-4 hrs; 2 hrs-3 hrs; 6 hrs-3 days; 6 hrs-2 days; 6 hrs-1 day; 6 hrs-18 hrs; 6 hrs-12 hrs; 6 hrs-8 hrs; 8 hrs-3 days; 8 hrs-2 days; 8 hrs-1 day; 8 hrs-18 hrs; 8 hrs-12 hrs; 8 hrs-10 hrs; 12 hrs-3 days; 12 hrs-2 days; 12 hrs-1 day; 12 hrs-18 hrs; 18 hrs-3 days; 18 hrs-2 days; 18 hrs-1 day; 1 day-3 days; or 2 days-3 days, for example. In specific embodiments, such incubation occurs for 1-8; 1-7; 1-6; 1-5; 1-4; 1-3; 1-2; 2-8; 2-7; 2-6; 2-5; 2-4; 2-3; 3-8; 3-7; 3-6; 3-5; 3-4; 4-8; 4-7; 4-6; 4-5; 5-8; 5-7; 5-6; 6-8; 6-7; or 7-8 hours, for example.

In certain embodiments, the fibroblasts are exposed to certain levels of CO. In particular embodiments, incubation of the fibroblasts with CO is performed at a concentration of at least or no more than 1-500 parts per million (ppm); 1-400 ppm; 1-300 ppm; 1-250 ppm; 1-200 ppm; 1-175 ppm; 1-150 ppm; 1-125 ppm; 1-100 ppm; 1-75 ppm; 1-50 ppm; 1-25 ppm; 1-10 ppm; 10-500 ppm; 10-400 ppm; 10-300 ppm; 10-250 ppm; 10-200 ppm; 10-150 ppm; 10-125 ppm; 10-100 ppm; 10-75 ppm; 10-50 ppm; 10-25 ppm; 25-500 ppm; 25-400 ppm; 25-300 ppm; 25-250 ppm; 25-200 ppm; 25-175 ppm; 25-150 ppm; 25-125 ppm; 25-100 ppm; 25-75 ppm; 25-50 ppm; 50-500 ppm; 50-400 ppm; 50-300 ppm; 50-200 ppm; 50-175 ppm; 50-150 ppm; 50-125 ppm; 50-100 ppm; 50-75 ppm; 75-500 ppm; 75-400 ppm; 75-300 ppm; 75-250 ppm; 75-225 ppm; 75-200 ppm; 75-175 ppm; 75-150 ppm; 75-125 ppm; 75-100 ppm; 100-500 ppm; 100-400 ppm; 100-300 ppm; 100-200 ppm; 100-150 ppm; 100-125 pm; 125-500 ppm; 125-400 ppm; 125-300 ppm; 125-275 ppm; 125-200 ppm; 125-175 ppm; 125-150 ppm; 150-500 ppm; 150-400 ppm; 150-300 ppm; 150-200 ppm; 150-175 ppm; 175-500 ppm; 175-400 ppm; 175-300 ppm; 175-275 ppm; 175-250 ppm; 175-225 ppm; 175-200 ppm; 200-500 ppm; 200-400 ppm; 200-300 ppm; 200-250 ppm; 250-500 ppm; 250-400 ppm; 250-300 ppm; 250-275 ppm; 300-500 ppm; 300-400 ppm; or 400-500 ppm, for example. In specific cases, incubation of fibroblasts with CO is performed at a concentration of 75, 100, 125, 150, 175, 200, 225, 250, 275, 300, or 325 or more parts per million (ppm) for 1, 2, 3, 4, 5, 6, 7, 8, 9, or 10 or more hours.

In particular embodiments, the fibroblasts are exposed to a particular level of CO as described above for a particular period of time, such as at least or no more than between 30 minutes (min)-3 days; 30 min-2 days; 30 min-1 days; 30 min-18 hours (hrs); 30 min-12 hrs; 30 min-8 hrs; 30 min-6 hrs; 30 min-4 hrs; 30 min-2 hrs; 30 min-1 hr; 45 min-3 days; 45 min-2 days; 45 min-1 days; 45 min-18 hrs; 45 min-12 hrs; 45 min-8 hrs; 45 min-6 hrs; 45 min-4 hrs; 45 min-2 hrs; 45 min-1 hr; 60 min-3 days; 60 min-2 days; 60 min-1 days; 60 min-18 hrs; 60 min-12 hrs; 60 min-8 hrs; 60 min-6 hrs; 60 min-4 hrs; 60 min-2 hrs; 60 min-1 hr; 2 hrs-3 days; 2 hrs-2 days; 2 hrs-1 days; 2 hrs-18 hrs; 2 hrs-12 hrs; 2 hrs-8 hrs; 2 hrs-6 hrs; 2 hrs-4 hrs; 2 hrs-3 hrs; 6 hrs-3 days; 6 hrs-2 days; 6 hrs-1 day; 6 hrs-18 hrs; 6 hrs-12 hrs; 6 hrs-8 hrs; 8 hrs-3 days; 8 hrs-2 days; 8 hrs-1 day; 8 hrs-18 hrs; 8 hrs-12 hrs; 8 hrs-10 hrs; 12 hrs-3 days; 12 hrs-2 days; 12 hrs-1 day; 12 hrs-18 hrs; 18 hrs-3 days; 18 hrs-2 days; 18 hrs-1 day; 1 day-3 days; or 2 days-3 days, for example. In specific embodiments, such incubation occurs for 1-8; 1-7; 1-6; 1-5; 1-4; 1-3; 1-2; 2-8; 2-7; 2-6; 2-5; 2-4; 2-3; 3-8; 3-7; 3-6; 3-5; 3-4; 4-8; 4-7; 4-6; 4-5; 5-8; 5-7; 5-6; 6-8; 6-7; or 7-8 hours, for example.

In particular embodiments, the cells are treated with hypoxia prior to treatment with CO, although in other embodiments the cells are treated with hypoxia during and/or after treatment with CO. In certain embodiments, there is a synergistic effect on the fibroblasts (for example, synergistic growth factor production by the fibroblasts) upon sequential exposure of the cells to hypoxia followed by CO treatment.

In particular embodiments, the disclosure provides methods of augmenting therapeutic activity of fibroblasts through modification of culture conditions for the fibroblasts. In specific embodiments, there are previously undisclosed synergies in terms of stimulation of regenerative activity by culture of fibroblasts in hypoxia, together with low concentrations of carbon monoxide. In one embodiment, fibroblasts are exposed to one or more agents and/or one or more culture conditions for the purpose of the fibroblasts producing a conditioned media comprising one or more factors and/or other agent(s) for a therapeutic application.

In specific cases, the fibroblasts (following exposure to one or more particular agents and/or culture conditions) are utilized as a source of conditioned media; in certain cases the conditioned media comprises one or more particular growth factors or other agent(s). In specific embodiments, conditioned media produced by the fibroblasts is stored for future use or the media may be used without first being stored. In some cases, the fibroblasts produce a conditioned media and the media is provided to the individual from which the fibroblasts were obtained. In other cases the fibroblasts produce a conditioned media and the media is provided to the individual other than the one from which the fibroblasts were obtained. The conditioned media may be generated in a patient-specific context (using autologous fibroblasts) or universal donor context (using allogenic fibroblasts).

In specific embodiments, the fibroblast-conditioned media may be utilized for any application, including acceleration of wound healing, induction of angiogenesis, and/or for cosmetic means, as examples. In specific embodiments, fibroblasts are exposed to conditions augmenting regenerative properties and administered to an individual as a supplement or substitute to stem cells, including mesenchymal stem cells. In one embodiment, fibroblasts are injected at a particular site in an individual, including intradiscally for stimulation of disc regeneration. Augmentation of fibroblast regenerative activity as disclosed herein may be achieved by a two-step process involving an initial exposure to hypoxia, followed by exposure to conditions stimulating HO-1, such as CO, in certain cases.

In one aspect of the disclosure, potency of the conditioned media product from the fibroblasts may be analyzed. In specific embodiments, the conditioned media may be analyzed for assessing protein production, for example. Such assays are well-known to one of skill in the art.

The conditioned media may be analyzed for anti-inflammatory activity, for example the conditioned media may have anti-inflammatory activity so that it can be used as an anti-inflammatory agent or with one or more other anti-inflammatory agents. For quantification of anti-inflammatory activity, the term "inflammation" will be understood by those skilled in the art to include any condition characterized by a localized or a systemic protective response, which may be elicited by physical trauma, infection, chronic diseases, and/or chemical and/or physiological reactions to external stimuli (e.g., as part of an allergic response). Any such response, which may serve to destroy, dilute or sequester both the injurious agent and the injured tissue, may be manifested by, for example, heat, swelling, pain, redness, dilation of blood vessels and/or increased blood flow, invasion of the affected area by white blood cells, loss of function and/or any other symptoms known to be associated with inflammatory conditions. The term "inflammation" will thus also be understood to include any inflammatory disease, disorder or condition per se, any condition that has an inflammatory component associated with it, and/or any condition characterized by inflammation as a symptom, including, inter alia, acute, chronic, ulcerative, specific, allergic and necrotic inflammation, and other forms of inflammation known to those skilled in the art. The term thus also includes, for the purposes of this disclosure, inflammatory pain and/or fever caused by inflammation.

In one embodiment, conditioned media is generated in an ex-vivo extracorporeal setting. Specifically, fibroblast cells of interest are grown extracorporeally, such as on and/or in one or more substrates. In a specific embodiment the cells are grown on the outside of a hollow-fiber filter, for example that is connected to a continuous extracorporeal system. The hollow-fiber system contains pores in the hollow fiber of sufficient size so as to allow exchange of proteins between circulating blood cells and cultured cells on the outside of the hollow fibers, without interchange of host cells with the fibroblast cells. In one embodiment, fibroblast-conditioned media is used in combination with one or more immune suppressive agents to augment its activity.

While fibroblast-conditioned media may or may not be used alone for treatment and/or maintenance of disease remission, in some embodiments administration of one or more immune suppressive agents may be utilized in certain methods. Additionally, an immune suppressive agent may be useful for "induction therapy". Depending on disease and response desired, it will be known to one of skill in the art to choose from various immune suppressive agents. For example, some immune suppressive agents, such as anti-CD52 antibodies, may be used when a systemic depletion of T and B cells is desired, whereas agents that concurrently stimulate T regulatory cell activity, such as Rapamycin, may be desired in other cases. The skilled practitioner is guided to examples of several agents that are known in the art for causing immune suppression, which include cyclosporine, rapamycin, campath-1H, ATG, Prograf, anti IL-2r, MMF, FTY, LEA, cyclosporin A, diftitox, denileukin, levamisole, azathioprine, brequinar, gusperimus, 6-mercaptopurine, mizoribine, rapamycin, tacrolimus (FK-506), folic acid analogs (e.g., denopterin, edatrexate, methotrexate, piritrexim, pteropterin, Tomudex®, and trimetrexate), purine analogs (e.g., cladribine, fludarabine, 6-mercaptopurine, thiamiprine, and thiaguanine), pyrimidine analogs (e.g., ancitabine, azacitidine, 6-azauridine, carmofur, cytarabine, doxifluridine, emitefur, enocitabine, floxuridine, fluorouracil, gemcitabine, and tegafur) fluocinolone, triaminolone, anecortave acetate, fluorometholone, medrysone, prednislone, etc. In another embodiment, the use of stem cell conditioned media may be used to potentiate an existing anti-inflammatory agent. Anti-inflammatory agents may comprise one or more agents including NSAIDs, interleukin-1 antagonists, dihydroorotate synthase inhibitors, p38 MAP kinase inhibitors, TNF-alpha inhibitors, TNF-alpha sequestration agents, and methotrexate. More specifically, anti-inflammatory agents may comprise one or more of, e.g., anti-TNF-alpha, lysophylline, alpha 1-antitrypsin (AAT), interleukin-10 (IL-10), pentoxyfilline, COX-2 inhibitors, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., ampiroxicam, droxicam, isoxicam, lornoxicam, piroxicam, tenoxicam), epsilon.-acetamidocaproic acid, s-adenosylmethionine, 3-amino-4-hydroxybutyric .acid, amixetrine, bendazac, benzydamine, .alpha.-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, zileuton, candelilla wax, alpha bisabolol, aloe vera, Manjistha, Guggal, kola extract, chamomile, sea whip extract, glycyrrhetic acid, glycyrrhizic acid, oil soluble licorice extract, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, disodium 3-succinyloxy-beta-glycyrrhetinate, or a combination thereof.

The fibroblasts utilized in the disclosure may be generated, in one embodiment, by outgrowth from a biopsy of the recipient's own skin (in the case of autologous preparations), or skin of one or more healthy donors (for allogeneic preparations). In some embodiments fibroblasts are used from young donors, although the donor may be of any age, including newborn, infant, child, adolescent, adult, or elderly. In another embodiment fibroblasts are transfected with one or more genes. In specific examples, the fibroblasts are transfected with one or more genes to allow for enhanced growth and overcoming of the Hayflick limit. Examples of such genes includes telomerase, hTERT, and/or one or more oncogenes, such as RAS, c-myc, RAF, or bcr-able. Subsequent to derivation of cells, the fibroblasts may be expanded in culture using standard cell culture techniques. Skin tissue (dermis and epidermis layers) may be biopsied from a subject's post-auricular area, in some cases. In one embodiment, the starting material is comprised of multiple 3-mm punch skin biopsies collected using standard aseptic practices. The biopsies may be collected by a medical practitioner and placed into a vessel comprising a suitable buffer, such as a vial comprising sterile phosphate buffered saline (PBS). The biopsies may be transported prior to use, such as transported at a suitable temperature (for example, 2-8° C.). The biopsies may be transported suitably to a manufacturing facility. In one embodiment, after arrival at the manufacturing facility, a biopsy may be inspected and, upon acceptance, transferred directly to a manufacturing area.

Upon initiation of the process of preparing the cells, the biopsy tissue may be washed, such as washed prior to enzymatic digestion. After washing, enzymes may be exposed to the tissue, such as mixtures of collagenase and/or neutral protease enzymes (for example, Liberase™ Digestive Enzyme Solution (Lonza Walkersville, Inc. (Walkersville, Md.) or Roche Diagnostics Corp. (Indianapolis, Ind.)) being added to the tissue with or without mincing, and the biopsy tissue is then incubated at suitable temperature and duration, such as 37.0±2° C. for one hour. Time of biopsy tissue digestion is a process parameter that can affect the viability and growth rate of cells in culture. Alternatively to Liberase™, other commercially available collagenases may be used, such as Serva Collagenase NB6 (Helidelburg, Germany). After digestion, suitable media may be provided to the digested material, such as Initiation Growth Media (IMDM, GA, 10% Fetal Bovine Serum (FBS)) that may be added to neutralize the enzyme. The cells may be pelleted, such as by centrifugation, and re-suspended in 5.0 mL Initiation Growth Media. Alternatively, centrifugation is not performed, with full inactivation of the enzyme occurring by the addition of media (such as Initiation Growth Media) only. Initiation Growth Media may be added prior to seeding of the cell suspension into suitable vessel, such as a T-175 cell culture flask for initiation of cell growth and expansion. In some cases, T-75, T-150, T-185 or T-225 flask can be used in place of the T-75 flask. Cells are incubated at 37±2.0° C. with 5.0±1.0% $CO_2$ and fed with fresh media, such as Complete Growth Media, at a suitable interval, such as every three to five days. Feeds in the process may be performed by removing a fraction (such as about half) of the media (such as Complete Growth Media) and replacing the same volume with fresh media. Alternatively, full feeds can be performed. In one embodiment, cells are not left in the flask greater than a certain number of days prior to passaging, such as about 30 days and may be left at least 24 hours prior to passaging. Confluence is monitored throughout the process to ensure adequate seeding densities during culture splitting. When cell confluence is greater than or equal to a certain percentage (such as about 40%-about 70%) in the vessel, the cells may be passaged by removing the spent media, washing the cells, and treating with Trypsin-EDTA to release adherent cells in the flask into the solution. Cells may then be trypsinized and seeded into a suitable vessel (T-500 flask, for example) for continued cell expansion. Alternately, one or two T-300 flasks, One Layer Cell Stack (1 CS), One Layer Cell Factory (1 CF) or a Two Layer Cell Stack (2 CS) can be used in place of the T-500 Flask. Morphology may be evaluated at each passage and prior to harvest to monitor the culture purity throughout the process. Morphology may be evaluated by comparing the observed sample with visual standards for morphology examination of cell cultures, for example. The cells display typical fibroblast morphologies when growing in cultured monolayers. Cells may display either an elongated, fusiform or spindle appearance with slender extensions, or appear as larger, flattened stellate cells that may have cytoplasmic leading edges. A mixture of these morphologies may also be observed. Fibroblasts in less confluent areas can be similarly shaped, but randomly oriented. The presence of keratinocytes in cell cultures may also be evaluated. Keratinocytes appear round and irregularly shaped and, at higher confluence, they appear organized in a cobblestone formation. At lower confluence, keratinocytes are observable in small colonies. Cells are incubated at 37±2.0° C. with 5.0±1.0% $CO_2$ and passaged every three to five days in the T-500 flask and every five to seven days in the ten layer cell stack (10CS). Cells should not remain in the T-500 flask for more than 10 days prior to passaging, in some embodiments. Quality Control (QC) release testing for safety of the Bulk Drug Substance includes sterility and endotoxin testing. When cell confluence in the T-500 flask is approximately 95%, cells are passed to a 10 CS culture vessel. Alternately, two Five Layer Cell Stacks (5 CS) or a 10 Layer Cell Factory (10 CF) can be used in place of the 10 CS. 10CS. Passage to the 10 CS is performed by removing the spent media, washing the cells, and treating with Trypsin-EDTA to release adherent cells in the flask into the solution. Cells are then transferred to the 10 CS. Additional Complete Growth Media is added to neutralize the trypsin and the cells from the T-500 flask are pipetted into a 2 L bottle containing fresh Complete Growth Media. The contents of the 2 L bottle are transferred into the 10 CS and seeded across all layers. Cells are then incubated at 37±2.0° C. with 5.0±1.0% $CO_2$ and fed with fresh Complete Growth Media every five to seven days. Cells should not remain in the 10CS for more than 20 days prior to passaging, in particular embodiments. In one embodiment, the passaged dermal fibroblasts are rendered substantially free of immunogenic proteins present in the culture medium by incubating the expanded fibroblasts for a period of time in protein free medium, Primary Harvest When cell confluence in the 10 CS is 95% or more, cells are harvested. Harvesting may be performed by removing the spent media, washing the cells, treating with Trypsin-EDTA to release adherent cells into the solution, and adding additional Complete Growth Media to neutralize the trypsin. Cells may be collected by centrifugation, re-suspended, and in-process QC testing performed to determine total viable cell count and cell viability.

In some embodiments, when large numbers of cells are required after receiving cell count results from the primary 10 CS harvest, an additional passage into multiple cell stacks (up to four 10 CS) may be performed. For additional passaging, cells from the primary harvest are added to a 2 L media bottle containing fresh Complete Growth Media. Resuspended cells are added to multiple cell stacks and incubated at 37±2.0° C. with 5.0±1.0% $CO_2$. The cell stacks are fed and harvested as described above, except cell confluence is 80% or higher prior to cell harvest, in certain embodiments. The harvest procedure may be the same as described for the primary harvest above. A mycoplasma sample from cells and spent media is collected, and cell count and viability performed as described for the primary harvest above. The method decreases or eliminates immunogenic proteins by avoiding their introduction from animal-sourced reagents. To reduce process residuals, cells are cryopreserved in protein-free freeze media, then thawed and washed prior to prepping the final injection to further reduce remaining residuals. If additional Drug Substance is needed after the harvest and cryopreservation of cells from additional passaging is complete, aliquots of frozen Drug Substance—Cryovial are thawed and used to seed 5 CS or 10 CS culture vessels. Alternatively, a four layer cell factory (4 CF), two 4 CF, or two 5 CS can be used in place of a 5 CS or 10 CS. A frozen cryovial(s) of cells is thawed, washed, added to a 2 L media bottle containing fresh Complete Growth Media and cultured, harvested and cryopreserved as described above. The cell suspension is added Cell confluence must be 80% or more prior to cell harvest.

At the completion of culture expansion, the cells are harvested and washed, then formulated to contain 1.0-2.7× $10^7$ cells/mL, with a target of 2.2×$10^7$ cells/mL. Alternatively, the target can be adjusted within the formulation range to accommodate different indication doses. The drug substance comprises a population of viable, autologous human fibroblast cells suspended in a suitable medium, such as a cryopreservation medium comprised of Iscove's Modified Dulbecco's Medium (IMDM) and Profreeze-CDM™ (Lonza, Walkerville, Md.) plus 7.5% dimethyl sulfoxide (DMSO). Alternatively, a lower DMSO concentration may be used in place of 7.5% or CryoStor™ CS5 or CryoStor™ CS10 (BioLife Solutions, Bothell, Wash.) may be used in place of IMDM/Profreeze/DMSO. In addition to cell count and viability, purity/identity of the Drug Substance is performed and must confirm the suspension contains 98% or more fibroblasts. The usual cell contaminants include keratinocytes. The purity/identify assay employs fluorescent-tagged antibodies against CD90 and CD 104 (cell surface markers for fibroblast and keratinocyte cells, respectively) to quantify the percent purity of a fibroblast cell population. CD90 (Thy-1) is a 35 kDa cell-surface glycoprotein. Antibodies against CD90 protein have been shown to exhibit high specificity to human fibroblast cells. CD104, integrin .beta.4 chain, is a 205 kDa transmembrane glycoprotein which associates with integrin .alpha.6 chain (CD49f) to form the alpha6/beta4 complex. This complex has been shown to act as a molecular marker for keratinocyte cells (Adams and Watt 1991).

Antibodies to CD 104 protein bind to 100% of human fibroblast cells. Cell count and viability is determined by incubating the samples with Viacount Dye Reagent and analyzing samples using the Guava PCA system. The reagent is composed of two dyes, a membrane-permeable dye which stains all nucleated cells, and a membrane-impermeable dye which stains only damaged or dying cells. The use of this dye combination enables the Guava PCA system to estimate the total number of cells present in the sample, and to determine which cells are viable, apoptotic, or dead. The method was custom developed specifically for use in determining purity/identity of autologous cultured fibroblasts. Alternatively, cells can be passaged from either the T-175 flask (or alternatives) or the T-500 flask (or alternatives) into a spinner flask containing microcarriers as the cell growth surface. Microcarriers are small bead-like structures that are used as a growth surface for anchorage dependent cells in suspension culture. They are designed to produce large cell yields in small volumes. In this apparatus, a volume of Complete Growth Media ranging from 50 mL-300 mL is added to a 500 mL, IL or 2 L sterile disposable spinner flask. Sterile microcarriers are added to the spinner flask. The culture is allowed to remain static or is placed on a stir plate at a low RPM (15-30 RRM) for a short period of time (1-24 hours) in a 37±2.0° C. with 5.0±1.0% $CO_2$ incubator to allow for adherence of cells to the carriers. After the attachment period, the speed of the spin plate is increased (30-120 RPM). Cells are fed with fresh Complete Growth Media every one to five days, or when media appears spent by color change. Cells are collected at regular intervals by sampling the microcarriers, isolating the cells and performing cell count and viability analysis. The concentration of cells per carrier is used to determine when to scale-up the culture. When enough cells are produced, cells are washed with PBS and harvested from the microcarriers using trypsin-EDTA and seeded back into the spinner flask in a larger amount of microcarriers and higher volume of Complete Growth Media (300 mL-2 L). Alternatively, additional microcarriers and Complete Growth Media can be added directly to the spinner flask containing the existing microcarrier culture, allowing for direct bead-to-bead transfer of cells without the use of trypsinizationtrypsiziation and reseeding. Alternatively, if enough cells are produced from the initial T-175 or T-500 flask, the cells can be directly seeded into the scale-up amount of microcarriers. After the attachment period, the speed of the spin plate is increased (30-120 RPM). Cells are fed with fresh Complete Growth Media every one to five days, or when media appears spent by color change. When the concentration reaches the desired cell count for the intended indication, the cells are washed with PBS and harvested using trypsin-EDTA. Microcarriers used within the disposable spinner flask may be made from poly blend such as BioNOC II® (Cesco Bioengineering, distributed by Bellco Biotechnology, Vineland, N.J.) and FibraCel® (New Brunswick Scientific, Edison, N.J.), gelatin, such as Cultispher-G (Percell Biolytica, Astrop, Sweden), cellulose, such as Cytopore™. (GE Healthcare, Piscataway, N.J.) or coated/uncoated polystyrene, such as 2D MicroHex™. (Nunc, Weisbaden, Germany), Cytodex® (GE Healthcare, Piscataway, N.J.) or Hy-Q Sphere™ (Thermo Scientific Hyclone, Logan, Utah).

In another embodiment, cells can be processed on poly blend 2D microcarriers such as BioNOC II® and FibraCel® using an automatic bellow system, such as FibraStage™ (New Brunswick Scientific, Edison, N.J.) or BelloCell® (Cesco Bioengineering, distributed by Bellco Biotechnology, Vineland, N.J.) in place of the spinner flask apparatus. Cells from the T-175 (or alternatives) or T-500 flask (or alternatives) may be passaged into a bellow bottle containing microcarriers with the appropriate amount of Complete Growth Media, and placed into the system. The system pumps media over the microcarriers to feed cells, and draws away media to allow for oxygenation in a repeating fixed cycle. Cells are monitored, fed, washed and harvested in the same sequence as described above. Alternatively, cells can be processed using automated systems. After digestion of the biopsy tissue or after the first passage is complete (T-175 flask or alternative), cells may be seeded into an automated device. One method is an Automated Cellular Expansion (ACE) system, which is a series of commercially available or custom fabricated components linked together to form a cell growth platform in which cells can be expanded without human intervention. Cells are expanded in a cell tower, consisting of a stack of disks capable of supporting anchorage-dependent cell attachment. The system automatically circulates media and performs trypsinization for harvest upon completion of the cell expansion stage.

Alternatively, the ACE system can be a scaled down, single lot unit version comprised of a disposable component that consists of cell growth surface, delivery tubing, media and reagents, and a permanent base that houses mechanics and computer processing capabilities for heating/cooling, media transfer and execution of the automated programming cycle. Upon receipt, each sterile irradiated ACE disposable unit will be unwrapped from its packaging and loaded with media and reagents by hanging pre-filled bags and connecting the bags to the existing tubing via aseptic connectors. The process continues as follows: a) Inside a biological safety cabinet (BSC), a suspension of cells from a biopsy that has been enzymatically digested is introduced into the "pre-growth chamber" (small unit on top of the cell tower), which is already filled with Initiation Growth Media containing antibiotics. From the BSC, the disposable would be transferred to the permanent ACE unit already in place; b) After approximately three days, the cells within the pre-growth chamber are trypsinized and introduced into the cell tower itself, which is pre-filled with Complete Growth Media. Here, the "bubbling action" caused by $CO_2$ injection force the media to circulate at such a rate that the cells spiral downward and settle on the surface of the discs in an evenly distributed manner; c) For approximately seven days, the cells are allowed to multiply. At this time, confluence will be checked (method unknown at time of writing) to verify that culture is growing. Also at this time, the Complete Growth Media will be replaced with fresh Complete Growth Media. CGM may be replaced at suitable intervals, such as every seven days for three to four weeks. At the end of the culture period, the confluence is checked once more to verify that there is sufficient growth to possibly yield the desired quantity of cells for the intended treatment; d) If the culture is sufficiently confluent, it is harvested. The spent media (supernatant) is drained from the vessel. PBS will then is pumped into the vessel (to wash the media, FBS from the cells) and drained almost immediately. Trypsin-EDTA is pumped into the vessel to detach the cells from the growth surface. The trypsin/cell mixture is drained from the vessel and enter the spin separator. Cryopreservative is pumped into the vessel to rinse any residual cells from the surface of the discs, and be sent to the spin separator as well. The spin separator collects the cells and then evenly resuspend the cells in the shipping/injection medium. From the spin separator, the cells will be sent through an inline automated cell counting device or a sample collected for cell count and viability testing via laboratory analyses. Once a specific number of cells has been counted and the proper cell concentration has been reached, the harvested cells are delivered to a collection vial that can be removed to aliquot the samples for cryogenic freezing.

In another embodiment, automated robotic systems may be used to perform cell feeding, passaging, and harvesting for the entire length or a portion of the process. Cells can be introduced into the robotic device directly after digest and seed into the T-175 flask (or alternative). The device may have the capacity to incubate cells, perform cell count and viability analysis and perform feeds and transfers to larger culture vessels. The system may also have a computerized cataloging function to track individual lots. Existing technologies or customized systems may be used for the robotic option.

In one embodiment, fibroblasts are pre-activated before exposure to hypoxia/carbon monoxide by contact with one or more growth factors, such as in a mixture, including a growth factor containing mixture. The mixture may comprise growth factor(s) selected from the group consisting of transforming growth factors (TGF), fibroblast growth factors (FGF), platelet-derived growth factors (PDGF), epidermal growth factors (EGF), vascular endothelial growth factors (VEGF), insulin-like growth factors (IGF), platelet-derived endothelial growth factors (PDEGF), platelet-derived angiogenesis factors (PDAF), platelet factors 4 (PF-4), hepatocyte growth factors (HGF), and mixtures thereof. In specific embodiments, the growth factors are transforming growth factors (TGF), platelet-derived growth factors (PDGF), fibroblast growth factors (FGF), or mixtures thereof. In particular embodiments, the growth factor(s) are selected from the group consisting of transforming growth factors beta (TGF-beta), platelet-derived growth factors BB (PDGF-BB), basic fibroblast growth factors (bFGF), and mixtures thereof. In another embodiment of the disclosure, growth factor—comprising compositions are provided simultaneously with, or subsequent to, delivery of fibroblasts, either or both of which may be injected. The fibroblasts may be autologous, allogeneic, or xenogeneic. In some embodiments a platelet plasma composition is administered together with the fibroblasts or separately from the fibroblasts, for example subsequent to administration of the fibroblasts. A platelet plasma composition may comprise, consist essentially of, or consist of platelets and plasma and may be derived from bone marrow or peripheral blood, for example. The present disclosure may use platelet plasma compositions from either or both of these sources, and either platelet plasma composition may be used to regenerate either a nucleus or annulus in need thereof. Further, a platelet plasma composition may be used with or without concentrated bone marrow (BMAC). By way of example, when inserted into the annulus, 0.05-2.0 cc of platelet plasma composition may be used, and when inserted into the nucleus, 0.05-3.0 cc of the platelet plasma composition may be used. Platelets are non-nucleated blood cells that as noted above are found in bone marrow and peripheral blood. They have several important functions such as controlling bleeding and tissue healing. As persons of ordinary skill in the art are aware, the ability to promote tissue healing is due to the many growth factors that they produce, including platelet-derived growth factor (PDGF), transforming growth factor beta (TGF-beta), fibroblast growth factor (FGF), insulin-like growth factor-1 (IGF-1), connective tissue growth factor (CTGF) and/or vascular endothelial growth factor (VEGF).

II. Methods of Use of the Fibroblasts

Embodiments of the disclosure include prepared fibroblasts for a therapeutic purpose for an individual, and in some cases conditioned media from the fibroblasts is provided to an individual in addition to or alternative to the prepared fibroblasts.

Following preparation of the fibroblasts as encompassed herein such that their regenerative activity is enhanced, a suitable number of fibroblasts are provided to one or more individuals in need thereof, including multiple deliveries where necessary. The disclosure includes methods of generating a therapeutic product through growth of fibroblast populations in a liquid media and providing same to one or more individuals in need thereof. In one embodiment, there are methods of generating a medicament comprising prepared fibroblasts and/or conditioned media useful for the treatment of at least one medical condition, including at least inflammatory, autoimmune, and/or degenerative conditions. In specific embodiments, the fibroblasts are prepared through culturing of the fibroblasts such that they are exposed to hypoxia and/or CO at suitable levels and suitable exposures. In some cases, the hypoxia condition may first be provided to the fibroblasts followed by carbon monoxide, both at a concentration and time of exposure sufficient in specific cases to stimulate HIF-1 alpha and heme-oxygenase, for example respectively.

Many types of media may be used by one of skill in the art to prepare the conditioned media. In one embodiment, a media is selected from a group comprising of alpha MEM, DMEM, RPMI, Opti-MEM, IMEM, and AIM-V. Cells may be cultured in a variety of media for expansion that may or may not contain fetal calf serum or other growth factors; however, for collection of therapeutic supernatant, in a particular embodiment, the cells are transferred to a media substantially lacking serum. In some embodiments, the conditioned medium may be provided directly to an individual in need of treatment. It is well known in the art that preparation of the conditioned medium before administration may be performed by various means; for example, the conditioned medium may be filter sterilized, or in some conditions concentrated. In a particular embodiment, the conditioned medium is administrated for induction of regenerative activities, alone, or in combination with cells possessing regenerative properties.

In some embodiments, the prepared cells and/or conditioned media are utilized for methods of promoting healing of wounds by administering cultured fibroblasts and/or conditioned media therefrom. Examples of wounds include epithelial wounds and/or fistula. In certain embodiments, there are methods of augmenting tissue sub-adjacent to a vocal cord defect for an individual by administering cultured fibroblasts and/or conditioned media therefrom. In certain embodiments, the prepared cells and/or conditioned media are utilized for a method of treatment of vocal fold scarring and/or repair of skin and soft tissue defects, such as fibrotic damage, inflammation damage, atrophy, and/or burn damage.

The prepared fibroblasts, which in specific embodiments are HO-1 augmented, are useful for a variety of therapeutic indications, in many situations analogous for which stem cells, including mesenchymal stem cells, would be useful. Examples of the amount of cells that may be provided to an individual include a range of 10,000/kg to 300 million/kg.

In some embodiments, conditioned media is used as an active ingredient for a pharmaceutical formulation, either alone or with fibroblasts. This may comprise administration of the hypoxic/carbon monoxide fibroblast cell-conditioned media therapeutic agent alone, but in some cases comprises administration by way of known pharmaceutical formulations, including tablets, capsules or elixirs for oral administration, suppositories for rectal administration, sterile solutions or suspensions for parenteral or intramuscular administration, liposomal or encapsulated formulations, formulations wherein a therapeutic agent is alone or conjugated to a delivery agent or vehicle, and the like. It will be appreciated that therapeutic entities of the disclosure (including prepared fibroblasts) may be administered with suitable carriers, excipients, and/or other agents that are incorporated into formulations to provide improved transfer, delivery, tolerance, and the like. A multitude of appropriate formulations can be found in the formulary known to all pharmaceutical chemists: Remington's Pharmaceutical Sciences (15$^{th}$ ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Powell et al. "Compendium of excipients for parenteral formulations" PDA J Pharm Sci Technol 52:238-311 (1998) and the citations therein for additional information related to excipients and carriers well known to pharmaceutical chemists. In one embodiment of the disclosure, one or more agents of the disclosure are nanoencapsulated into nanoparticles for delivery. The nanoencapsulation material may be biodegradable or nondegradable. The nanoencapsulation materials may be made of synthetic polymers, natural polymers, oligomers, or monomers. Synthetic polymers, oligomers, and monomers include those derived from polyalkyleneoxide precursor molecules, such as poly(ethylene oxide) (PEO), poly(ethylene glycol) (PEG) and copolymers with poly(propylene oxide) (PEG-co-PPO), poly (vinyl alcohol) (PVA), poly(vinylpyrrolidone) (PVP), poly(ethyloxazoline) (PEOX), polyaminoacids, and pseudopolyamino acids, and copolymers of these polymers. Sawhney et al., Macromolecules 26:581-587 (1993). Copolymers may also be formed with other water-soluble polymers or water insoluble polymers, provided that the conjugate is water soluble. An example of a water-soluble conjugate is a block copolymer of polyethylene glycol and polypropylene oxide, commercially available as a Pluronic™ surfactant (BASF). Natural polymers, oligomers and monomers include proteins, such as fibrinogen, fibrin, gelatin, collagen, elastin, zein, and albumin, whether produced from natural or recombinant sources, and polysaccharides, such as agarose, alginate, hyaluronic acid, chondroitin sulfate, dextran, dextran sulfate, heparin, heparin sulfate, heparan sulfate, chitosan, gellan gum, xanthan gum, guar gum, water soluble cellulose derivatives, and carrageen. These polymers are merely exemplary of the types of nanoencapsulation materials that can be utilized and are not intended to represent all the nanoencapsulation materials within which entrapment is possible. In one embodiment, the therapeutic agent is administered in a topical formulation. Topical formulations are useful in the treatment of conditions associated with dermal diseases. For example, topical administration of fibroblast cell-conditioned media and/or the prepared fibroblasts may be performed for the treatment of psoriasis, scleroderma, or acne. Topical forms of administration may consist of, for example, aqueous and nonaqueous gels, creams, multiple emulsions, microemulsions, liposomes, ointments, aqueous and nonaqueous solutions, lotions, aerosols, skin patches, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer. Topical formulations of the invention may include a dermatologically acceptable carrier, e.g., a substance that is capable of delivering the other components of the formulation to the skin with acceptable application or absorption of those components by the skin. The carrier will typically include a solvent to dissolve or disperse the therapeutic agent, and, optionally one or more excipients or other vehicle ingredients. Carriers useful in accordance with the topical formulations of the present invention may include, by way of non-limiting example, water, acetone, ethanol, ethylene glycol, propylene glycol, butane-1,3-diol, acrylates copolymers, isopropyl myristate, isopropyl palmitate, mineral oil, butter(s), aloe, talc, botanical oils, botanical juices, botanical extracts, botanical powders, other botanical derivatives, lanolin, urea, petroleum preparations, tar preparations, plant or animal fats, plant or animal oils, soaps, triglycerides, and keratin(s). Topical formulations of the invention are prepared by mixing a compound of the invention with a topical carrier according to well-known methods in the art, for example, methods provided by standard reference texts e.g., Remington: The Science and Practice of Pharmacy, 1577-1591, 1672-1673, 866-885 (Alfonso R. Gennaro ed. 19th ed. 1995); and Ghosh et al., Transdermal and Topical Drug Delivery Systems (1997). In other embodiments, moisturizers or humectants, sunscreens, fragrances, dyes, and/or thickening agents such as paraffin, jojoba, PABA, and waxes, surfactants, occlusives, hygroscopic agents, emulsifiers, emollients, lipid-free cleansers, antioxidants and lipophilic agents, may be added to the topical formulations of the invention if desired. A topical formulation of the media and/or cells of the disclosure may be designed to be left on the skin and not washed shortly after application. Alternatively, the topical formulation may be designed to be rinsed off within a given amount of time after application.

In one embodiment, the treatment of one or more immunological diseases is performed by administration of the hypoxic/carbon monoxide fibroblast-treated conditioned media and/or the prepared fibroblasts directly to its site(s) of therapeutic activity, which in the case of many immune diseases is in the lymph nodes. For example, the therapeutic agent may be injected directly into the lymph nodes. Preferred lymph nodes for intranodal injections of inhibitors of T cell-dependent activation are the major lymph nodes located in the regions of the groin, the underarm and the neck. In another embodiment, the therapeutic agent is administered distal to the site of its therapeutic activity.

In specific embodiments, a medical conditions treated with prepared fibroblasts and/or conditioned media therefrom include autoimmune diseases, degenerative diseases, inflammatory diseases, and fibrotic diseases. Examples of autoimmune diseases are Graves' disease, lupus, type I diabetes, multiple sclerosis, rheumatoid arthritis, and so on. Examples of degenerative diseases are degenerative disc disease, Alzheimer's disease, cancer, Charcot-Marie—Tooth disease, type II diabetes, heart disease, muscular dystrophy, Parkinson's disease, Huntington's disease, macular degeneration, spinal muscular atrophy, Inflammatory bowel disease, osteoporosis, osteoarthritis, Tay-Sachs disease, primary pulmonary hypertension, and so on. Examples of inflammatory diseases (that can be chronic or acute) include asthma, tuberculosis, ulcerative colitis, chronic peptic ulcer, periodontitis, Crohn's disease, sinusitis, and so on. Examples of fibrotic disease include Pulmonary fibrosis, radiation-induced lung injury, cirrhosis, atrial fibrosis, endomyocardial fibrosis, glial scar, keloid, myelofibrosis, scleroderma, and so on.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synergistic Stimulation of VEGF Production by Culture of Fibroblasts in Hypoxia, Carbon Monoxide, or Hypoxia Followed by Carbon Monoxide Foreskin fibroblasts purchased from ATCC where cultured in T-75 flasks using Fibroblast Basal Media from ATCC. When cells reached 75% confluence, exposure to: a) Normoxia; b) hypoxia (2% oxygen for 4 hours); c) carbon monoxide (250 ppm) for 4 hours; or d) hypoxia followed by carbon monoxide. Cells were re-plated on 96 well plates, flat bottomed, by trypsinization. Concentration of re-plated cells was 0, 10,000, 20,000 and 40,000 cells per well. Culture media was extracted after 24 hours of culture and analyzed for VEGF production using ELISA (R&D Systems). As seen in FIG. 1, a synergistic increase in VEGF production was observed by the combined treatments. No VEGF production was observed from Normoxic Control fibroblasts.

Example 2

Figure 2:
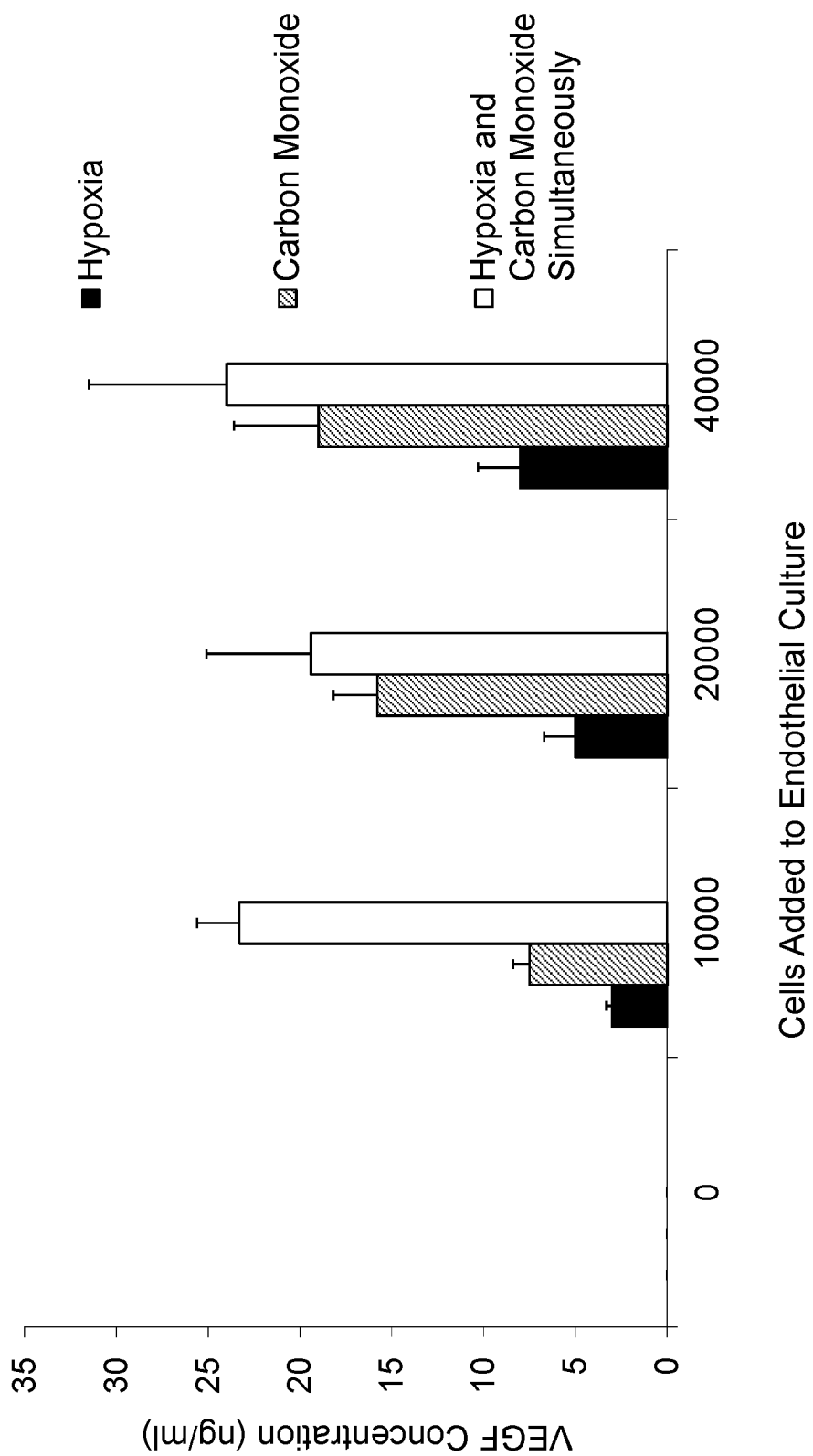
FIG. 2 shows stimulation of VEGF production by culture of fibroblasts with hypoxia, carbon monoxide, or hypoxia concurrent with carbon monoxide.

Stimulation of VEGF Production by Culture of Fibroblasts in Hypoxia, Carbon Monoxide, or Hypoxia Concurrent with Carbon Monoxide Foreskin fibroblasts purchased from ATCC where cultured in T-75 flasks using Fibroblast Basal Media from ATCC. When cells reached 75% confluence, exposure to: a) Normoxia; b) hypoxia (2% oxygen for 4 hours); c) carbon monoxide (250 ppm) for 4 hours; or d) hypoxia simultaneously as carbon monoxide Cells were replated on 96 well plates, flat bottomed, by trypsinization. Concentration of replated cells was 0, 10,000, 20,000 and 40,000 cells per well. Culture media was extracted after 24 hours of culture and analyzed for VEGF production using ELISA (R&D Systems). As seen in FIG. 2, a synergistic increase in VEGF production was observed by the combined treatments. No VEGF production was observed from Normoxic Control fibroblasts. These data suggest the carbon monoxide exposure synergizes with hypoxia for augmentation of VEGF production.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method of enhancing a therapeutic activity of a plurality of fibroblasts, comprising the step of providing to the fibroblasts an effective amount of a combination of hypoxia and carbon monoxide.

2. The method of claim 1, wherein the therapeutic activity comprises regenerative activity of the fibroblasts.

3. The method of claim 1, wherein the fibroblasts have an increase in secretion of one or more cytokines and/or growth factors.

4. The method of claim 1, wherein the fibroblasts have an increase in anti-apoptotic activity.

5. The method of claim 1, wherein the immunogenicity of the fibroblasts is modulated.

6. The method of claim 1, wherein the carbon monoxide is provided to the fibroblasts subsequent to the hypoxia.

7. The method of claim 1, wherein the carbon monoxide is provided to the fibroblasts at the same time as the hypoxia.

8. The method of claim 1, wherein an effective amount of the fibroblasts is provided to an individual.

9. The method of claim 8, wherein the individual has an autoimmune disease, degenerative disease, inflammatory disease, and/or a fibrotic disease.

10. The method of claim 8, wherein the conditioned medium comprises one or more growth factors and/or one or more cytokines.

11. The method of claim 1, wherein the hypoxia is 0.1%-10%, 0.1%-5%, 0.1%-2.5%, or 0.1%4% oxygen.

12. The method of claim 1, wherein the hypoxia occurs for a period of time that is such as at least or no more than between 30 minutes-3 days.

13. The method of claim 1, wherein the fibroblasts are exposed to one or more growth factors prior to exposure to the hypoxia, carbon monoxide, or a combination thereof.

14. The method of claim 1, further comprising obtaining a conditioned medium from the fibroblasts.

15. The method of claim 14, wherein an effective amount of the fibroblasts and/or the conditioned medium is provided to an individual.

16. The method of claim 15, wherein the individual has an autoimmune disease, degenerative disease, inflammatory disease, and/or a fibrotic disease.

17. The method of claim 15, wherein the conditioned medium comprises one or more growth factors and/or one or more cytokines.

* * * * *

UNITED STATES PATENT AND TRADEMARK OFFICE
CERTIFICATE OF CORRECTION

| | |
|---|---|
| PATENT NO. | : 11,959,102 B2 |
| APPLICATION NO. | : 16/770495 |
| DATED | : April 16, 2024 |
| INVENTOR(S) | : Pete O'Heeron and Thomas Ichim |

It is certified that error appears in the above-identified patent and that said Letters Patent is hereby corrected as shown below:

In the Claims

In Claim 11, Column 20, Line 25, please replace "or 0.1%4% oxygen" with --or 0.1%-1% oxygen-- therefor.

Signed and Sealed this
Twenty-eighth Day of May, 2024

*Katherine Kelly Vidal*

Katherine Kelly Vidal
*Director of the United States Patent and Trademark Office*